US00PP35786P2

(12) United States Plant Patent
Van Swieten

(10) Patent No.: US PP35,786 P2
(45) Date of Patent: Apr. 30, 2024

(54) ***PHALAENOPSIS* ORCHID PLANT NAMED 'PHA312391'**

(50) Latin Name: ***Phalaenopsis* hybrid**
Varietal Denomination: PHA312391

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,049

(22) Filed: Mar. 17, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — Jondle & Associates, P.C.

(57) ABSTRACT

A new and distinct variety of *Phalaenopsis* plant named 'PHA312391', particularly characterized by having small white flowers with greenish-yellow and white lips, flowers that are flat in lateral view, erect leaf attitude, and is propagated by meristem tissue culture, is disclosed.

3 Drawing Sheets

Genus and species: *Phalaenopsis* hybrid.
Variety denomination: 'PHA312391'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA312391'.

The new *Phalaenopsis* plant is a product of a planned breeding program conducted by the inventor in Bleiswijk, the Netherlands. The objective of this breeding program was to create a new *Phalaenopsis* plant with numerous attractive, small, white flowers with greenish-yellow and white lips, suitable for potted plant production.

The new *Phalaenopsis* plant 'PHA312391' is a result of cross-pollination made by the inventor in August 2012 in Bleiswijk, the Netherlands, of the proprietary female, or seed parent, *Phalaenopsis* hybrid '07-000001-3479' (unpatented) with the proprietary male, or pollen parent, *Phalaenopsis* hybrid '07-030896-0012' (unpatented).

The new *Phalaenopsis* was selected by the inventor as a single plant within the progeny of the stated cross-pollination in a controlled greenhouse in Bleiswijk, the Netherlands, in June 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1095), by Applicant who obtained the subject matter disclosed directly from the inventor. 'PHA312391' has not been made publicly available or sold anywhere in the world prior to the effective filing date of this application with the exception of sales or disclosures made one year or less before the effective filing date of this claimed invention by Applicant who obtained 'PHA312391' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA312391' as a new and distinct variety of *Phalaenopsis* plant:

1) Small, white flowers with greenish-yellow and white lips;
2) Flower shape in lateral view is flat; and
3) Leaf attitude is erect.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in December 2022. Colors in the photographs may differ from the color values cited in the detailed botanical description, which accurately describe the actual colors of the new variety.

DESCRIPTION OF THE NEW VARIETY

Figure 1:
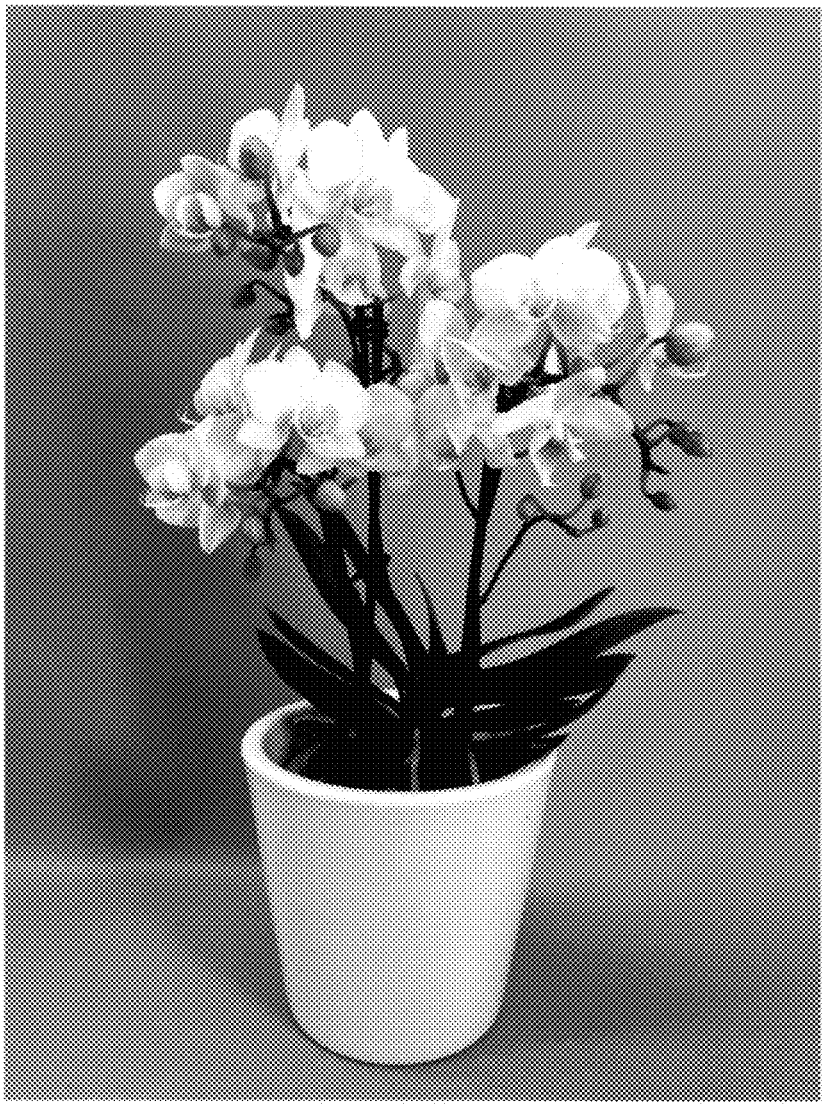
FIG. 1 shows the overall plant habit, including blooms, buds, and foliage of 'PHA312391'.
Figure 2:
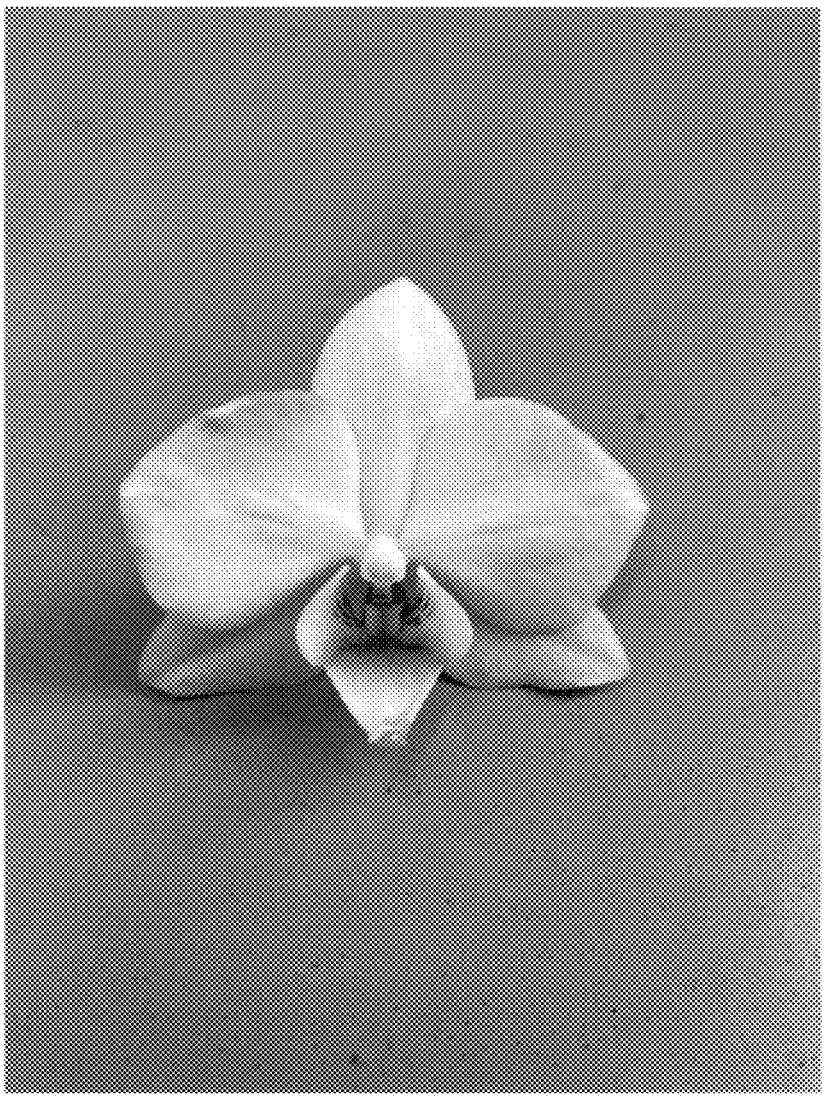
FIG. 2 shows a close-up of a flower of 'PHA312391'.
Figure 3:
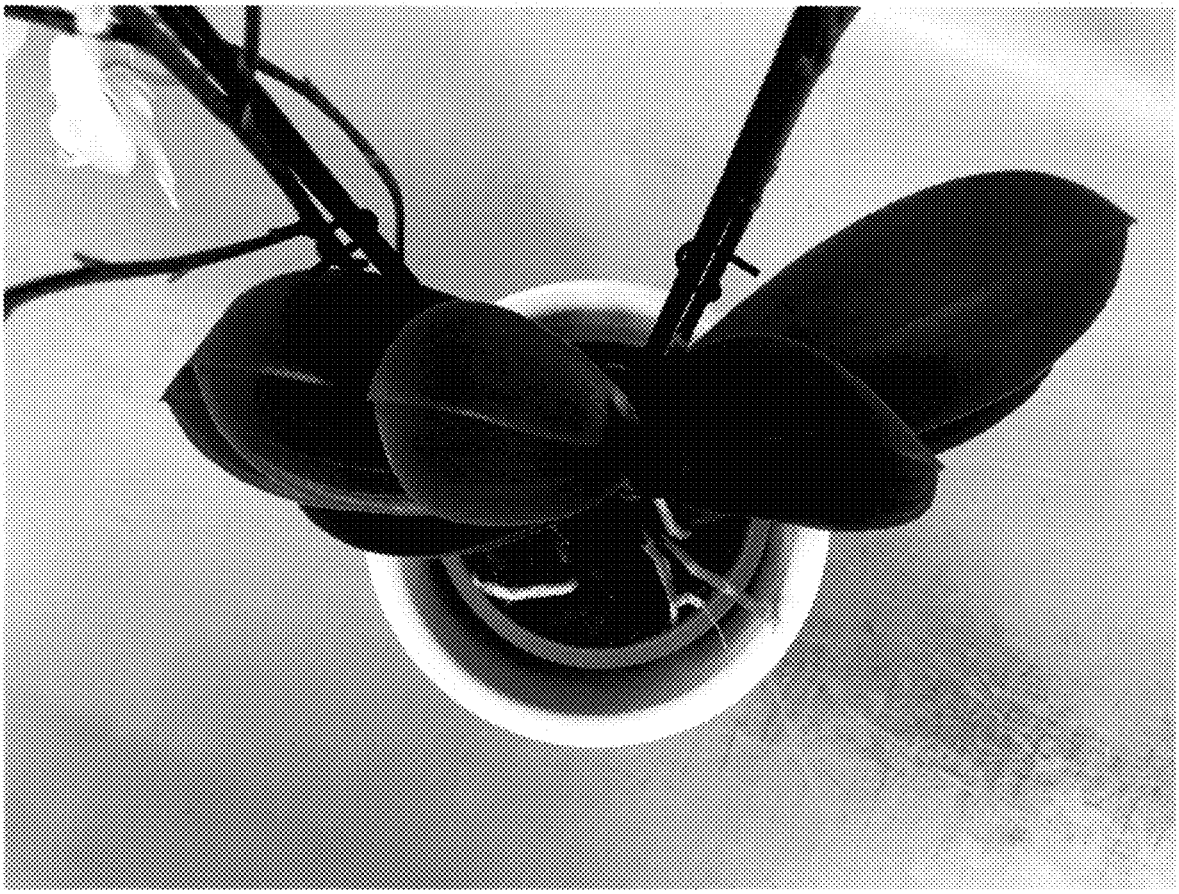
FIG. 3 shows an overhead, close-up view of the leaves of 'PHA312391'.

The following detailed description sets forth the distinctive characteristics of 'PHA312391'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA312391'.

Parentage:

*Female parent*.—*Phalaenopsis* cultivar '07-000001-3479' (unpatented).

*Male parent*.—*Phalaenopsis* cultivar '07-030896-0012' (unpatented).

Propagation:

*Type*.—Meristem tissue culture.

Roots:

*Root description*.—Greyed-green colored roots (a color in between RHS 190B and RHS 190C) with branching lateral roots having yellow-green (RHS 144B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 29.0 cm to 34.0 cm.

*Width* (*measured from leaf tips*).—About 21.0 cm to 23.0 cm.

*Vigor*.—Strong.

Leaves:

*Mature leaves*.—Quantity per plant: 14 to 17 leaves are produced before flowering. Length (fully expanded): 11.0 cm to 13.0 cm. Width: 5.0 cm to 6.0 cm. Position of the broadest part of the leaf: At the middle. Shape: Oblong. Base shape: Slightly elongated. Apex: Obtuse asymmetric. Leaf blade angle with the petiole (measured from the horizontal position): Between 30 degrees and 50 degrees. Leaf margin: Entire. Color: Upper surface: RHS 147A. Lower surface: RHS 147B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 147B.

Peduncle:

*Quantity per plant*.—2 to 3.

*Number of flowers per peduncle*.—12 to 17.

*Length*.—29.0 cm to 34.0 cm.

*Diameter*.—3.0 mm to 4.0 mm.

*Strength*.—Strong.

*Aspect*.—Upright to slightly pendent.

*Texture*.—Smooth.

*Color*.—Green (a mix of RHS 147B and RHS 147C).

*Internode length*.—2.0 cm to 3.0 cm.

Inflorescence description:

*Appearance*.—Upright to slightly pendent, panicle inflorescence with bilaterally symmetrical flowers that open in succession beginning with the lowermost flower.

*Number of inflorescences*.—2 to 3.

*Inflorescence size*.—Height (from base to tip): 140.0 mm to 190.0 mm.

*Flowering time*.—First flowers can be expected 10 to 11 months after planting in a 12-cm pot.

*Flower*.—Height: 40.0 mm to 45.0 mm. Diameter: 47.0 mm to 52.0 mm. Depth of lip: 17.0 mm to 19.0 mm.

*Flower shape*.—Flat.

*Flower longevity*.—On the plant: 11 to 13 weeks.

*Fragrance*.—Absent.

*Flower bud*.—Average size: Medium. Length: 14.0 mm to 16.0 mm. Width: 12.0 mm to 14.0 mm. Shape: Egg shaped. Color: Yellow-green (RHS N144D).

*Petals*.—Arrangement: Open/free. Shape: Semi-circular. Apex: Obtuse asymmetric. Margin: Weakly undulated. Length (from base to tip): 22.0 mm to 24.0 mm. Width: 23.0 mm to 25.0 mm. Position of the broadest part of the petal: Toward the base. Color (when fully opened): Upper surface: Basic color: White (RHS NN155C). Over color: Absent. Lower surface: Basic color: White (RHS NN155D). Over color: Absent. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 23.0 mm to 25.0 mm. Width: 14.0 mm to 16.0 mm. Position of the broadest part of the dorsal sepals: At the middle. Color (when fully opened): Upper surface: Basic color: White (RHS NN155C). Over color: Absent. Lower surface: Basic color: White (RHS NN155D). Over color: Touch of very light purple (RHS 76B) and light yellow-green (RHS 145D). Number of spots and stripes on the dorsal sepals (upper surface): None. Color of spots and stripes on the dorsal sepals (upper surface): Not applicable. Density of netting of the dorsal sepals (upper surface): None. Color of the netting (upper surface): Not applicable.

*Lateral sepals*.—Shape: Ovate. Apex: Obtuse asymmetric. Margin: Weakly undulated. Length (from base to tip): 23.0 mm to 25.0 mm. Width: 14.0 mm to 16.0 mm. Position of the broadest part of the lateral sepals: Toward the base. Color (when fully opened): Upper surface: Basic color: White (RHS NN155C). Over color: Yellow-greenish shade on one side (RHS 145C). Lower surface: Basic color: White (RHS NN155D). Over color: Very light purple (RHS 76B) and light yellow-greenish shade on one side (RHS 145D). Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 8.0 mm to 10.0 mm. Color of whiskers: White (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 13.0 mm to 15.0 mm. Width: 9.0 mm to 11.0 mm. Color: Upper surface: White (RHS NN155C) and RHS 187D stripes at the base; greenish-yellow (RHS 151C) margin on one side from base toward the tip. Lower surface: White (RHS NN155C); greenish-yellow (RHS 151D) margin on one side toward the tip. Number of spots and stripes on the lateral lobe: Few to several stripes. Color of spots and stripes on the lateral lobe: RHS 187D. Density of netting of the lateral lobe: None. Color of the netting: None.

*Apical lobe*.—Shape: Triangular. Margin: Entire. Length: 14.0 mm to 16.0 mm. Width: 10.0 mm to 12.0 mm. Color: Upper surface: Reddish-brown (RHS 176B) very small dots at the margin, at the base, and greenish-yellow (RHS 151C) at the base; white (RHS NN155C) toward whiskers. Lower surface: Orange-brown (RHS 176B) margin and greenish-yellow (RHS 151D) at the base; white (RHS NN155D) toward whiskers. Number of spots and stripes on the apical lobe: Many very small dots. Color of spots and stripes on the apical lobe: RHS 176B. Density of netting of the apical lobe: None. Color of the netting: None. Bump and ridge: Absent.

*Callus*.—Average size: Small. Height: 3.0 mm to 4.0 mm. Length: 3.0 mm to 4.0 mm. Width: 2.0 mm to 3.0 mm. Color: Yellow (RHS 17B); RHS 59B very small dots.

Reproductive organs:

*Column*.—Length: 7.0 mm to 8.0 mm. Diameter: 3.0 mm to 4.0 mm. Color: White (RHS NN155C).

*Pollinia*.—Quantity: 2. Diameter: 0.6 mm to 0.8 mm. Color: Orange-yellow (RHS 23A).

*Ovary*.—Length: 5.0 mm to 7.0 mm. Diameter: 1.3 mm to 1.5 mm.

*Pedicel*.—Length: 24.0 mm to 26.0 mm. Diameter: 1.5 mm to 1.7 mm. Color: Yellow-green (RHS 145A) at the base; light yellow-green (RHS 145C) with a touch of very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA312391' differs from the female parent plant '07-000001-3479' (unpatented) in that 'PHA312391' has slightly elongated mature leaves, erect leaf attitude, and the lower side of the dorsal sepal is very light purple and light yellow-green, whereas '07-000001-3479' has moderately elongated mature leaves, horizontal to semi-drooping leaf attitude, and the lower side of the dorsal sepal is light reddish-purple.

'PHA312391' differs from the male parent plant '07-030896-0012' (unpatented) in that 'PHA312391' has white whiskers, obtuse apexes, and the lower side of the dorsal sepal is very light purple and light yellow-green, whereas '07-030896-0012' has light greenish-yellow whiskers, rounded apexes, and the lower side of the dorsal sepal is light yellow-green.

'PHA312391' is most similar to the commercial *Phalaenopsis* plants named 'PHALGUOCH' (U.S. Plant Pat. No. 32,281) and 'PHALDRIDOP' (U.S. Plant Pat. No. 28,980). 'PHA312391' differs from the commercial variety 'PHALGUOCH' in that 'PHA312391' has triangular apical lobes, erect leaf attitude, and does not have spots on the lateral sepals, whereas 'PHALGUOCH' has ovate apical lobes, horizontal to semi-drooping leaf attitude, and medium spots on the lateral sepals.

'PHA312391' differs from the commercial variety 'PHALDRIDOP' in that 'PHA312391' has narrow leaves with erect attitude and obtuse mature leaf apexes, whereas 'PHALDRIDOP' has narrow to medium leaves with semi-erect to horizontal attitude and rounded mature leaf apexes.

I claim:

1. A new and distinct variety of *Phalaenopsis* plant named 'PHA312391', substantially as described and illustrated herein.

* * * * *